(12) United States Patent
Choi et al.

(10) Patent No.: US 8,728,514 B2
(45) Date of Patent: May 20, 2014

(54) TRANSDERMAL PREPARATIONS CONTAINING HYDROPHOIC NON-STEROIDAL ANTI-INFLAMMATORY DRUGS

(75) Inventors: Yang Gyu Choi, Yongin (KR); Young Chang Ah, Yongin (KR); Woo Jeong Choi, Seongnam (KR); Jung Ju Kim, Yongin (KR)

(73) Assignee: Pacific Pharmaceutical Co., Ltd., Seoul (KR)

( * ) Notice: Subject to any disclaimer, the term of this patent is extended or adjusted under 35 U.S.C. 154(b) by 1047 days.

(21) Appl. No.: 12/084,014

(22) PCT Filed: Oct. 23, 2006

(86) PCT No.: PCT/KR2006/004330
§ 371 (c)(1),
(2), (4) Date: Apr. 22, 2008

(87) PCT Pub. No.: WO2007/049892
PCT Pub. Date: May 3, 2007

(65) Prior Publication Data
US 2009/0252782 A1    Oct. 8, 2009

(30) Foreign Application Priority Data
Oct. 24, 2005    (KR) .................. 10-2005-0100164

(51) Int. Cl.
*A61K 9/70* (2006.01)
(52) U.S. Cl.
USPC ........................................... 424/449
(58) Field of Classification Search
CPC combination set(s) only.
See application file for complete search history.

(56) References Cited

U.S. PATENT DOCUMENTS

| | | | | |
|---|---|---|---|---|
| 3,972,995 A | * | 8/1976 | Tsuk et al. | 424/435 |
| 4,307,075 A | * | 12/1981 | Martin | 424/435 |
| 4,695,465 A | * | 9/1987 | Kigasawa et al. | 424/449 |
| 4,746,515 A | * | 5/1988 | Cheng et al. | 424/449 |
| 5,505,956 A | * | 4/1996 | Kim et al. | 424/448 |
| 5,702,720 A | | 12/1997 | Effing et al. | |
| 6,190,690 B1 | | 2/2001 | Park et al. | |
| 6,262,121 B1 | * | 7/2001 | Kawaji et al. | 514/567 |
| 6,676,962 B1 | | 1/2004 | Muller | |

FOREIGN PATENT DOCUMENTS

| | | | | |
|---|---|---|---|---|
| EP | 0340307 | * | 11/1989 | A61K 9/70 |
| EP | 0 698 393 A1 | | 2/1996 | |
| EP | 0 887 075 A2 | | 5/1998 | |
| KR | 10-0188180 | | 1/1999 | |
| KR | 10-0213465 | | 5/1999 | |
| KR | 10-2002-0035451 | | 5/2002 | |
| KR | 10-2003/0034692 | | 5/2003 | |
| WO | WO 02/36103 A1 | | 5/2002 | |
| WO | WO 2005/123046 A1 | | 6/2005 | |

OTHER PUBLICATIONS

Shojaei, "Buccal Mucosa As A Route for Systemic Drug Delivery: A Review." *J. Pharm. Pharmaceut Sci.*, (1): 15-30, 1998.
Naik et al., "Transdermal drug delivery: overcoming the skin's barrier function." *PSIT*, vol. 3, No. 9, p. 318-326, Sep. 2000.

* cited by examiner

*Primary Examiner* — Sue Liu
*Assistant Examiner* — Jessica Kassa
(74) *Attorney, Agent, or Firm* — Merchant & Gould P.C.

(57) ABSTRACT

Disclosed is a transdermal preparation containing a hydrophobic drug. As a method of continuing the high drug permeation, it is used an unique hydrophilic polymer system in which the drug can be contained in a high concentration under no water environment, a solubility of the hydrophobic drug is decreased as the water is introduced to the patch from the skin, so that the drug is maintained at the saturation concentration even though the drug content is decreased as the drug is permeated to the skin. During the application of the transdermal preparation to the skin, it is possible to continuously permeate the high amount of drug, to maintain the sufficient adhesion during the use and to minimize the skin side effect, because the hydrophilic polymer absorbs the water from the skin. The hydrophilic polymer system can serve the function thereof through the hydrophobic adhesive layer capable of preventing the water quickly absorbed from the skin from being evaporated to the outside of the patch.

10 Claims, 1 Drawing Sheet

TRANSDERMAL PREPARATIONS CONTAINING HYDROPHOIC NON-STEROIDAL ANTI-INFLAMMATORY DRUGS

TECHNICAL FIELD

The present invention relates to a transdermal preparation allowing high-concentrated hydrophobic drugs to be continuously permeated into the skin. More specifically, the invention relates to a patch of a transdermal preparation containing non-steroidal anti-inflammatory drugs, in particular one of ketoprofen, diclofenac, flurbiprofen and felbinac. Particularly, the invention relates to a patch-type arthritis treatment agent.

BACKGROUND ART

Currently, for the purpose of treating the arthritis, a variety of transdermal preparations containing non-steroidal anti-inflammatory drugs such as ketoprofen, diclofenac, flurbiprofen, felbinac, piroxicam and the like were developed and are marketed. Many researches on the transdermal preparations are carried out to meet the market needs. Main research fields include a research on the permeation enhancement of drug for more rapid and effective treatment, a research on the decrease of skin trouble caused by a patch type product, a research on adhesive substances not causing pains when the patch is detached after use, and the like.

The typical transdermal preparations containing the non-steroidal anti-inflammatory drugs, which are used for the purpose of the arthritis treatment, can directly deliver the drug in an inflamed area. The transdermal preparations directly deliver the drug to a lesion to maintain a concentration in the synovial fluid, on which the drugs act, at $1/5 \sim 1/2$ of a level in the oral administration. Accordingly, the transdermal preparations exhibit the effects similar to the oral administration and the drug concentration in the blood is lower by about 100 times than the oral preparations, so that they do not cause the side effects such as gastrointestinal tract disorder. Owing to such advantages, the transdermal preparations containing the non-steroidal anti-inflammatory drugs are widely used. However, they are still considered to have the efficacies lower than the oral preparations. Therefore, if a concentration of drug in the lesion such as synovial fluid can be increased as much as the oral preparation by improving a drug permeation, it is possible to obtain a treatment effect same as that of the oral preparation without causing the side effects of the non-steroidal anti-inflammatory drugs such as gastrointestinal tract disorder, which is expected to be more effective for the arthritis treatment.

In the transdermal preparation fields of a drug-in-adhesive type, as technology for increasing the drug permeation, it is widely used a technology for using permeation enhancer to increase diffusion and distribution effects of the drug, containing the drug at a saturation concentration in a system to increase a chemical activity of the drug, or hydrating the skin to lower barrier function of skin for the drug, thereby easily diffusing the drug.

As a specific example, a Korean Patent No. 10-0213465 discloses a multi-layered patch for obtaining high drug permeability. The patch uses an elastic backing and comprises an adhesive layer for adhering the backing and a drug layer, the drug layer containing the drug of a high concentration adding polyvinyl pyrrolidone or ethylene-vinylacetate and an adhesive layer for providing an adhesion and controlling a drug release, thereby obtaining high drug permeability and the skin adhesion. However, it is not easy to produce such patch because it has a multi-layered structure. In addition, since the adhesive layers are separately provided to give the adhesion, the drug permeation is slow, thereby exhibiting the limited effect only.

A Korean Patent No. 10-0188180 discloses technologies for increasing the drug permeability into the skin using multi-layered structure that is composed acrylic adhesives having difference water-absorption capacity and each acrylic adhesives layer can be changed drug solubility by water discharged from skin.

According to one technology suggested, plural adhesive layers consisting of acrylic adhesives resins having different water-absorption capacity are adapted to contain the drug and an acrylic adhesive layer having a low water-absorption capacity is located at the lowest layer. Thereby, although the content of the drug is decreased as the initial drug is permeated into the skin, the water moves to the upper layer and decrease the drug solubility in the upper acrylic adhesive layer, so that the drug is supplied to the lowest layer by concentration gradation of drug. As a result, the drugs are continuously delivered to the skin.

According to another technology suggested in the above patent, the acrylic adhesive layer having a high water-absorption capacity is located at the lowest layer, the drug of a high concentration is initially permeated and the drug permeation is decreased as time goes by, so that the drug is constantly permeated into skin. According to the first technology, since only the acrylic adhesive layers having similar solubility for the drug are used, a concentration difference of drug between acrylic adhesives layers is small, so that a desired effect is little. In addition, the concentration difference of drug in the adhesive layers is decreased during long time storage, so that a desired effect cannot be achieved. According to the second technology, when the acrylic adhesive layer having a high water-absorption capacity is located at the lowest layer, the hydrophobic drug contained in the upper layer is not smoothly moved to lower layer, so that the high drug permeability cannot be obtained.

In addition, U.S. Pat. No. 6,676,962 discloses a transdermal preparation containing a non-steroidal anti-inflammatory drug having a carboxyl group as an active material, having a unidirectional or dual directional flexibility due to a backing inactive for the active agent and using an acrylic adhesives base. In particular, according to the technology suggested, in consideration of use convenience, the flexible woven-fabric, knitted fabric, non-woven fabric or flexible foam (PE, PVC, EVA) as a backing is adopted so that it is easily used in the joint region and it is possible to obtain the higher drug permeability when the foam is adopted.

According to U.S. Pat. No. 5,702,720, the polyvinyl pyrrolidone which is hydrophilic polymer is used so that the water, which is exuded from the skin, is easily discharged to the outside and the physical properties of the patch is not deteriorated. In particular, the polyvinyl pyrrolidone, which is hydrophilic polymer, is used so that the pain caused when the patch is detached is decreased and the cohesion for preventing the adhesives from being remained is increased, among the properties of the patch.

According to Korean Patent Un-examined Publication No. 2002-035451 disclosing a transdermal preparation containing the diclofenac diethylammonium, the polyvinyl pyrrolidone, which is hydrophilic polymer, is used to absorb the water discharged from the skin, such as sweat, thereby enabling the patch not to be easily detached during the attachment and preventing the adhesive from being remained when detaching the patch. In addition to the prior arts as mentioned above, many technologies are disclosed in the fields. However, it is still needed a patch achieving the high permeability of drug in a short time and maintaining the high permeability of drug to maximize the treatment effect, increasing an adaptive degree of a patient due to an optimized adhesion property and enabling the patch to be easily produced. The invention is provided to meet the requirements.

DISCLOSURE

Technical Problem

As described above, an object of one embodiment of the invention is to deliver the hydrophobic drug through the skin in a quick and effective method. Typically, the drug permeation through the skin exhibits a peak at a predetermined level or more and then gradually decreased due to loss of the drug. In order to solve the problem, an object of one embodiment of the invention is to provide a transdermal preparation enabling high amount of drug to be continuously permeated through the skin until a patch containing the drugs is detached from the skin.

Another object of one embodiment of the invention is to provide a transdermal preparation comprising a drug layer having an adhesion.

Still another object of one embodiment of the invention is to provide a transdermal preparation having skin side effects minimized.

Still yet another object of one embodiment of the invention is to maintain an optimized adhesion until a transdermal preparation is detached from the skin.

In addition, an object of one embodiment of the invention is to directly deliver a non-steroidal anti-inflammatory agent to a lesion in a high concentration, thereby quickly and effectively treating the arthritis.

Technical Solution

In order to achieve the above objects, there is provided a transdermal preparation of a layered structure for a hydrophobic drug, the preparation comprising:

a backing layer (1) located at the highest part of the layered structure and having a flexibility;

a hydrophobic adhesive layer (2) placed below the backing layer and containing a hydrophobic adhesives to prevent water absorbed from skin from being lost and the drug from being reverse-transferred;

a drug adhesive layer (3) placed below the hydrophobic adhesive layer and containing a hydrophobic drug, an acrylic adhesives for adhering the transdermal preparation to the skin and a hydrophilic polymer resin for promoting the water absorption from the skin; and a release layer (4) placed below the drug adhesive layer, protecting the drug adhesive layer until the transdermal preparation is used and released when the preparation is used.

Advantageous Effects

When the transdermal preparation of the invention is used, it is possible to provide a transdermal preparation capable of enabling the hydrophobic drug of a high concentration to be continuously absorbed through the skin until the patch is detached from the skin. The transdermal preparation of the invention can minimize the skin side effect and improve the adhesion.

DESCRIPTION OF DRAWINGS

The above and other objects, features and advantages of the present invention will be more apparent from the following detailed description taken in conjunction with the accompanying drawings, in which.

BEST MODE

Hereinafter, a preferred embodiment of the present invention will be described with reference to the accompanying drawings. In the following description of the present invention, a detailed description of known functions and configurations incorporated herein will be omitted when it may make the subject matter of the present invention rather unclear.

Figure 1:
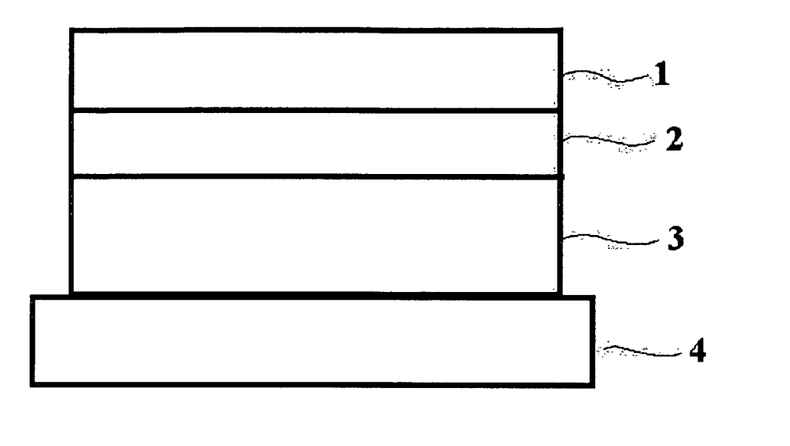
FIG. 1 is a schematic view showing a layered structure of a transdermal preparation according to an embodiment of the invention.

FIG. 1 shows a layered structure of a transdermal preparation according to an embodiment of the invention. A detailed description of each layer is as follows.

[Structure of the Transdermal Preparation of the Invention]

1) backing layer (1): it should have a flexibility for applying to a stretchable joint region.

2) hydrophobic adhesive layer (2): it is an adhesive layer having an liphophilic property and prevents the water exuded from the skin from volatilizing to maintain the water in the drug layer, thereby maintaining a chemical activity of the drug to the maximum.

3) drug adhesive layer (3): it comprises an acrylic adhesives for giving an adhesion, a drug, a hydrophilic polymer material having a high solubility for the drug under state that there is no water, such as polyvinyl pyrrolidone, so as to contain the drug in a high concentration, physical property adjustor (excipient, etc.) and the like.

4) release layer (4): it is provided to protect the drug adhesive layer 3 until the transdermal preparation is used.

1. Backing Layer (1)

The transdermal preparation containing the non-steroidal anti-inflammatory agent is used to treat musculoskeletal related diseases such as rheumatism, arthritis and the like. In particular, since the preparation is mainly used for the moveable joint region, a backing having a sufficient flexibility is used. The backing having the flexibility includes, but not limited to, woven or non-woven fabric of polyester based, polyvinyl based, urethane and cotton raw materials.

The transdermal preparation of the invention comprises the backing layer 1 made of the woven or non-woven fabric having a unidirectional or dual directional flexibility. The woven fabric consists of a polyester based resin, urethane based resin or cotton, and the non-woven fabric consists of the polyester based resin or urethane based resin. The woven or non-woven fabric made of the polyester based, polyurethane based or cotton raw material has a flexibility. However, since it has no occlusion effect, it is difficult to obtain an effect of preventing the drug from being reverse-absorbed and a thermal insulation effect. The transdermal preparation of the invention comprises the hydrophobic adhesive layer 2 below the backing layer 1. The hydrophobic adhesive layer 2 provides the occlusion effect, so that the above problems can be solved.

2. Hydrophobic Adhesive Layer 2

As described above, in the transdermal preparation of the invention, the hydrophobic adhesive layer 2 serves to complement the disadvantage of the backing layer 1 having the flexibility having no occlusion effect. In order to provide the occlusion effect, the hydrophobic adhesive layer 2 preferably comprises a polyisobutylene, styrene-isoprene-styrene based, or styrene-butadiene-styrene based adhesive. Owing to the occlusion effect, it is possible to prevent the drug from being reverse-transferred to the backing layer 1.

As a more important function, the hydrophobic adhesive layer 2 prevents the water, which has been absorbed in the drug adhesive layer 3 from the skin, from exuding to the outside, thereby maintaining the chemical activity of the drug in the drug adhesive layer 3 to the maximum. The drug adhesive layer 3 contains the drug in a high concentration before it is applied to the skin. From the application to the skin, as the water exuded from the skin is introduced into the drug adhesive layer 3, the solubility of the hydrophobic drug is slowly decreased, so that the drug is continuously present at the saturation concentration in the drug adhesive layer 3, thereby maintaining the drug permeation into the skin to the highest. Meanwhile, if the water introduced from the skin is discharged to the outside through the drug adhesive layer 3, the above effect cannot be obtained. Accordingly, in order to prevent this, the hydrophobic adhesive layer 2 is placed on the drug adhesive layer 3, thereby preventing the water from being discharged to the outside. Preferably, the hydrophobic adhesive layer 2 contains an adhesive having a very low solubility (less than 3%) for the drug, so as to prevent a back-diffusion of the drug. In other words, the above function of the drug adhesive layer 3 can be achieved only when the hydrophobic adhesive layer 2 prevents the water exudation.

Since the hydrophobic adhesive layer 2 also has a function of keeping the attachment part warm, it improves the blood circulation and the drug absorption. Since the polyisobutylene (PIB) based adhesive, styrene-isoprene-styrene (SIS) or styrene-butadiene-styrene (SBS) based adhesive and the like can be adapted to the movement of the joint region without disturbing the movement of the backing layer 1, it is preferable as an adhesive constituting the hydrophobic adhesive layer 2.

The adhesive, which can be used in the hydrophobic adhesive layer 2, has a basic structure made of one selected from polyisobutylene such as Vistanex MML100 (Mv 1,200,000) and MML 120 (Mv 1,600,000) available from an Exxon-Mobile company, and Oppanol B10SFN (Mv 40,000), B12SNF (Mv 55,000), B13SFN (Mv 65,000) and B15SFN (Mv 85,000) available from a BASF company, styrene-isoprene-styrene copolymer such as Kraton D1107, D1112 and D1113 (Shell Chemicals) and styrene-butadiene-styrene copolymer such as Kraton D1101 and D1102, and can additively contain a liquid phase component such as polymer resin, liquid paraffin and the like so as to complement the adhesion. A coating thickness of the hydrophobic adhesive layer 2 is preferably 40~100 μm. When the thickness of the coating of the hydrophobic adhesive layer 2 is less than 40 μm, the effect of suppressing the water discharge is low, and when the thickness is greater than 100 μm, the use feeling to the skin is low.

3. Drug Adhesive Layer 3

In the transdermal preparation for delivering the drug through the skin, an amount of the drug to be permeated can be expressed by a following equation 1.

$$\frac{dQ}{dT} = \frac{KC_M DA}{L} \qquad <\text{equation 1}>$$

where, dQ/dT: an amount of the drug permeated through the skin,
K: a distribution coefficient of the drug,
D: a diffusion coefficient of the drug,
$C_M$: a drug concentration in the patch,
A: an area of the patch, and
L: a thickness of the skin.

The distribution coefficient K of the equation 1 can be expressed by a ratio of a saturation concentration ($C_{SS}$) in the skin and a saturation concentration ($C_{SM}$) of the drug in the patch, i.e., equation 2.

$$K = \frac{C_{SS}}{C_{SM}} \qquad <\text{equation 2}>$$

When the equation 2 is substituted for the equation 1, a following equation 3 is obtained.

$$\frac{dQ}{dt} = \frac{DAC_{SS}}{L} \frac{C_M}{C_{SM}} \qquad <\text{equation 3}>$$

The skin permeation enhancer deteriorate a barrier function of the skin to diffuse the drug more easily, or increase a solubility of the drug in the skin to distribute the more drug to the skin, thereby increasing the drug permeation. In addition, it is possible to match a concentration of the drug in the patch to the saturation concentration, i.e., to make $C_M$ close to $C_{SM}$, thereby maximizing the drug permeation. However, as can be analogized from the equation 3, although the drug is under saturated state in the initial state of the patch, when the patch is attached to the skin and the drug begins to be permeated, the drug concentration in the patch is gradually decreased, so that the drug permeation is lowered as time goes by.

Accordingly, in order to maintain the drug permeation (released amount of the drug from the patch) to the skin from the patch containing the non-steroidal anti-inflammatory drug to the highest level during the attachment, the inventors attempted to maintain the drug concentration in the patch at the saturation concentration for the duration of an entire use.

According to the transdermal preparation of the invention, the hydrophilic polymers capable of containing a large quantity of drug such as ketoprofen, diclofenac, flurbiprofen and felbinac, for example polyvinyl pyrrolidone and polyethyleneglycol are added to the basic constituent materials such as adhesive, drug absorption promoter, drug and the like are added in order to maintain the drug at the saturation concentration in the patch while applying it to the skin, so that the drug becomes at the saturation concentration.

The above patch was prepared to apply it to an in vitro drug permeation and a human skin, and the drug permeation was checked. As a result, after the drug permeation reached a peak, it was maintained for 24 hours or more. This is caused by the following mechanism: a large quantity of the drug can be contained in the patch under state that there is no water, and the water can be quickly introduced from the skin when the patch is attached to the skin, thereby changing an environment into a hydrophilic environment due to the hydrophilic polymers. Therefore, the solubility of the hydrophobic drug is continuously slowly decreased, so that the drug can be continuously permeated to the skin in the high concentration during the attachment, thereby maintaining the drug permeation to the skin for a long time.

As described above, in case of a typical transdermal preparation, the drug permeation is high at early stage, but as time goes by, the drug is permeated into the skin, so that a concentration of the drug is lowered and the drug permeation to the skin is thus gradually decreased. In order to improve the problem, according to the invention, during the application to the skin, the drug is maintained at the saturation concentration in the drug adhesive layer 3 so that the chemical activity of the drug is maximized. In other words, under state that there is no water in the drug adhesive layer 3, the non-steroidal anti-inflammatory drugs such as ketoprofen is dissolved in a large quantity so that the drug can be much contained. However, when a patch is attached and then water is absorbed in the drug layer, a solubility of the hydrophobic drug is gradually decreased. Even though the drug concentration in the drug adhesive layer 3 becomes low continuously by the permeation of the drug through the skin, it is possible to maintain the chemical activity of the drug at the highest level, equally to the situation before using the patch. Such mechanism can be achieved by a hydrophilic polymer such as polyvinyl pyrrolidone (PVP) and polyethyleneglycol (PEG). In other words, the hydrophilic polymer is contained in a specific content to serve as unique dissolution agents that change the solubility of the drug depending on the water contents in the drug layer. The polyvinyl pyrrolidone or polyethyleneglycol can completely serve as the dissolution agents for the purpose of the invention through separate means for controlling the evaporation of the water absorbed. The separate means is the hydrophobic adhesive layer 2 consisting of the hydrophobic adhesive.

In the mean time, in order to contain the drug such as non-steroidal anti-inflammatory drug in the drug adhesive layer 3 in a high concentration, oil or surfactant may also be added in a large quantity, thereby achieving the object of the invention. However, in this case, although the large quantity of the drug can be contained in the patch, an affinity between the drug adhesive layer and the drug is high due to the oil or surfactant added in the drug adhesive layer 3, so that it has a negative influence on the drug permeation to the skin. In addition, when the oil or surfactant is used, the adhesion is lowered, as compared to a case where a polymer material is used. Further, when the patch is detached after completing the application, the adhesive can be remained at the skin.

In case that the water discharged from the skin is present between the patch and the skin, the patch may be detached while being applied to the skin, or skin irritation may be caused. However, according to the invention, the water discharged from the skin is absorbed to the drug adhesive layer, it is possible to solve the problems.

The hydrophilic polymer used for the invention includes the polyvinyl pyrrolidone (PVP) and polyethyleneglycol (PEG), which polymers can be used individually or mixed.

The polyvinyl pyrrolidone is preferably contained in an amount of 2~15 wt % for a total drug amount. When an amount of the polyvinyl pyrrolidone is less than 2 wt % for a total drug amount, the effect of promoting the water absorption from the skin is insufficient and the drug cannot be contained in the acrylic adhesives in a high concentration (20% or more). When the amount is more than 15 wt %, the affinity with the drug is excessive, so that the drug permeated to the skin from the patch is lowered, thereby decreasing the drug permeation to the skin. The polyvinyl pyrrolidone has preferably a molecular weight of 1,000~50,000, more preferably 2,000~30,000. When the molecular weight is less than 1,000, as time goes by after the patch was manufactured, there occurs a phase separation in the acrylic adhesives, so that the adhesion properties and the drug permeation can be lowered. When the molecular weight is more than 50,000, there occurs a problem of a compatibility with the acrylic adhesives, so that it is difficult to produce a uniform adhesive layer. A preferred example of the polyvinyl pyrrolidone is a polymer of a low-molecular weight (2,000~50,000) such as Kollidon 12 PF (Mw 2,000~3,000), 17 PF (Mw 7,000~11,000), 25 (Mw 28,000~34,000) and 30 (Mw 44,000~54,000) available from a BASF company.

The polyethyleneglycol is preferably contained in an amount of 10~20 wt % for a total drug amount. When an amount of the polyethyleneglycol is less than 10 wt % for a total drug amount, the effect of promoting the water absorption from the skin is insufficient. When the amount is more than 20 wt %, the drug permeation to the skin is lowered. The polyethyleneglycol has preferably a molecular weight of 400~8,000, more preferably 400~4,000. When the molecular weight is less than 400, as time goes by after the patch was manufactured, there occurs a phase separation, so that the adhesion properties and the drug permeation can be lowered. When the molecular weight is more than 8,000, there occurs a problem of a compatibility with the acrylic adhesives in the drug adhesive layer, so that it is difficult to produce a uniform adhesive layer. A preferred example of the polyethylene glycol includes PEG400 (Mw 380~420), PEG600 (Mw 570~630), PEG1000 (Mw 950~1050) and PEG4000 (Mw 3,600~4,400) available from a Dow Chemical company.

In addition, a content of the hydrophilic polymer resins is preferably 10 wt % or less for a total composition of the drug layer. When the content of the hydrophilic polymer resins is more than 10 wt %, cohesion of the adhesives is remarkably decreased, so that the adhesive may remain at the skin when using it or it is difficult to obtain a sufficient adhesion.

The acrylic adhesives included in the drug adhesive layer 3 serves as a drug-containing layer for containing the drug in the transdermal preparation. In addition, it serves to attach the patch to the skin so that the drug can be permeated through the skin. The acrylic adhesives used for the invention includes, but not limited to, DuroTak 87-2074, 2852, 2196, 2278 and 2510 (National Starch & Chemicals) and Gelva 737 and 788 (Solutia Co. Ltd.) which can be used in an individual or mixture form. A content of the acrylic adhesives in the drug adhesive layer 3 is preferably 40~80 wt % for a total composition of the drug adhesive layer, more preferably 50~70 wt %. When a content of the acrylic adhesives is less than 40 wt %, the adhesion to the skin is not sufficient.

When the content is more than 80 wt %, the amount of the drug is relatively decreased, so that the drug permeation is lowered.

The permeation enhancer is a long chain fatty acid having a carbon number of 10~18 and derivatives thereof and includes, for example, lauryl alcohol, oleyl alcohol, sorbitan monolaurate, polyethyleneglycol monolaurate, propyleneglycol monolaurate, glycerin monolaurate, caprylic monolaurate, isopropylmyristate and transcutol. The permeation enhancers can be used in an individual or mixture form.

The hydrophobic drug of the drug adhesive layer is preferably contained in an amount of 1~20 wt % for a total drug adhesive layer, more preferably 3~10 wt %. When an amount of the drug is less than 1 wt %, a drug efficacy is insufficient. When the amount is more than 20 wt %, the cohesive force of the adhesive layer is sharply decreased, so that the adhesive is remained at the skin when detaching the patch after the use thereof.

4. Release Layer 4

The release layer 4 is a layer placed below the drug adhesive layer 3 and protecting the drug adhesive layer 3 until the transdermal preparation is used. When applying to the skin, the layer is released. It is preferred that silicon or Teflon is coated on a polyester film or paper.

MODE FOR INVENTION

Hereinafter, embodiments of the invention will be more specifically described. However, it should be noted that the embodiments do not limit a scope of the invention defined in the claims.

EMBODIMENTS

Comparative Example 1

DuroTak 87-2074 8.0 g (National Starch & Chemicals), which is acrylic adhesive, (the used acrylic adhesives is a solution phase in which 30~40% solids are dissolved in a solvent such as ethylacetate, a weight of the adhesives was based on the solids, which will be omitted hereinafter), ketoprofen 1.5 g, and propyleneglycol monolaurate 0.5 g were put in a beaker and stirred for one hour to prepare a solution containing a drug having a uniform phase and then air bubbles were removed from the solution. The solution was coated on a silicon-treated polyester film 4 so as to have a thickness of 50 μm after drying and then dried at 80° C. for 20 minutes. After the drying, the drug adhesive layer 3 coated on the film 4 was covered with the backing 1 (flexible polyester woven fabric), which was then pressed with a roller, thereby producing a patch (20×40 $cm^2$).

Comparative Example 2

With regard to the adhesive layer containing a drug, Durotak 87-2074 6 g, DuroTak 87-2051 1 g (National Starch & Chemicals), ketoprofen 2.5 g, and glycerol monolaurate 0.5 g were put in a beaker and stirred for one hour to prepare a solution having a uniform phase and then air bubbles were removed from the solution. The solution was coated on a silicon-treated polyester film 4 so as to have a thickness of 50 μm after drying and then dried at 80° C. for 20 minutes. After that, the adhesive layer 3 coated on the film was covered with the backing 1 (flexible polyester non-woven fabric), which was then pressed with a roller, thereby producing a patch (20×40 $cm^2$).

Comparative Example 3

With regard to the hydrophobic adhesive layer 2 comprising a hydrophobic adhesives, Oppanol B12SNF (Mv 55,000) 5 g, which was polyisobutylene of a low-molecular weight, Vistanex MML100 (Mv 1,200,000) 2 g, which was polyisobutylene of a high-molecular weight, Sukroez Su-120 (Kolon) 3 g, which was hydrogenated petroleum resin, and hexane 30 Ml were put in a beaker and stirred to prepare a uniform solution. The solution was coated on a polyester film so as to have a thickness of 50 μm after drying and then dried at 60° C. for 10 minutes. After that, it was covered with the flexible backing 1 (flexible polyester woven fabric), which was then pressed with a roller. With respect to the drug adhesive layer 3 containing a drug, DuroTak 87-2074 6 g, which was an acrylic adhesives, Durotak 87-2051 1 g, ketoprofen 2.5 g, and glycerol monolaurate 0.5 g were put in a beaker and stirred for one hour to prepare a solution having a uniform phase and then air bubbles were removed from the solution. The solution was coated on a silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 $cm^2$).

Comparative Example 4

With regard to the drug adhesive layer 3 containing a drug, DuroTak 87-2074 6 g, which was an adhesive layer, ketoprofen 2.5 g, glycerol monolaurate 0.5 g, kollidon 17 PF 1 g (BASF, Mw 9,000) were put in a beaker and stirred for one hour to prepare a solution having a uniform phase and then air bubbles were removed from the solution. The solution was coated on a silicon-treated polyester film 4 so as to have a thickness of 50 μm after drying and then dried at 80° C. for 20 minutes. The prepared drug adhesive layer 3 was covered with the backing 1 (flexible polyester woven fabric), thereby producing a patch (20×40 $cm^2$).

Comparative Example 5

With respect to the hydrophobic adhesive layer 2, Oppanol B12SNF 5 g (Mv 55,000), which was polyisobutylene of a low-molecular weight, Vistanex MML100 2 g (Mv 1,200,000), which was polyisobutylene of a high-molecular weight, Regalite R 1100 3 g (Eastman company), which was hydrogenated petroleum resin, and hexane 30 Ml were put in a beaker and stirred to prepare a uniform solution. The solution was coated on a silicone-treated polyester film 4 so as to have a thickness of 50 μm after drying and then dried at 60° C. for 10 minutes. After that, the prepared hydrophobic adhesive layer 2 was covered with a flexible backing, which was then pressed with a roller. With respect to the drug adhesive layer 3 containing a drug, DuroTak 87-2074 6 g, which was an acrylic adhesives, ketoprofen 2.5 g, glycerol monolaurate 0.5 g and Kollidon 90F 1 g (BASF, Mw 1,000,000~1,500,000) were put in a beaker and stirred for one hour to prepare a solution having a uniform phase and then air bubbles were removed from the solution. The solution was coated on a silicon-treated polyester film 1 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 $cm^2$).

Comparative Example 6

With respect to the hydrophobic adhesive layer 2, Oppanol B12SNF 5 g (Mv 55,000), which was polyisobutylene of a low-molecular weight, Vistanex MML100 2 g (Mv 1,200,000), which was polyisobutylene of a high-molecular weight, Regalite R 1100 3 g (Eastman company), which was hydrogenated petroleum resin, and hexane 30 Ml were put in a beaker and stirred to prepare a uniform solution. The solution was coated on a silicone-treated polyester film so as to have a thickness of 30 μm after drying and then dried at 60° C. for 10 minutes. After that, the prepared hydrophobic adhesive layer 2 was covered with a flexible backing, which was then pressed with a roll. With regard to the drug adhesive layer 3 containing a drug, DuroTak 87-2852 6 g, which was an acrylic adhesives, ketoprofen 2.5 g, glycerol monolaurate 0.5 g and Kollidon 17 PF 1 g (BASF, Mw 7,000~11,000) were put in a beaker and stirred for one hour to prepare a solution having a uniform phase and then air bubbles were removed from the solution. The solution was coated on a silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 $cm^2$).

<Embodiment 1>

With respect to the hydrophobic adhesive layer 2, Oppanol B12SNF 5 g (Mv 55,000), which was polyisobutylene of a low-molecular weight, Vistanex MML100 2 g, which was polyisobutylene of a high-molecular weight, Regalite R 1100 3 g (Eastman company), which was hydrogenated petroleum resin, and hexane 30 Ml were put in a beaker and stirred to prepare a uniform solution. The solution was coated on a silicone-treated polyester film so as to have a thickness of 50 μm after drying and then dried at 60° C. for 10 minutes. After that, the prepared hydrophobic adhesive layer 2 was covered with the flexible backing 1, which was then pressed with a roller. With respect to the drug adhesive layer 3 containing a drug, DuroTak 87-2074 5.7 g, DuroTak 87-2051 1 g, which were acrylic adhesives, ketoprofen 2.5 g, propyleneglycol monolaurate 0.5 g and Kollidon 17 PF 0.3 g (BASF, Mw 7,000~11,000) were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 2>

The hydrophobic adhesive layer 2 was prepared with the same method as the embodiment 1. With respect to the drug adhesive layer 3 containing a drug, DuroTak 87-2074 6.4 g, which was an acrylic adhesives, ketoprofen 2.5 g, glycerol monolaurate 0.5 g and Kollidon 17 PF 0.6 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 3>

The hydrophobic adhesive layer 2 was prepared with the same method as the embodiment 1. With respect to the drug adhesive layer 3 containing a drug, DuroTak 87-2074 5.9 g, DuroTak 87-2051 1 g, which were acrylic adhesives, ketoprofen 2.5 g, glycerol monolaurate 0.5 g and Kollidon 17 PF 0.1 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 4>

The hydrophobic adhesive layer 2 was prepared to have a thickness of 40 μm with the same method as the embodiment 1. With respect to the drug adhesive layer 3 containing a drug, DuroTak 87-2852 6.7 g, which was an acrylic adhesives, ketoprofen 2.5 g, glycerol monolaurate 0.5 g and Kollidon 30 (BASF, Mw 44,000~54,000) 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 5>

The hydrophobic adhesive layer 2 was prepared with the same method as the embodiment 1. With respect to the drug adhesive layer 3 containing a drug, DuroTak 87-2074 3.7 g, DuroTak 87-2852 3 g, which were acrylic adhesives, ketoprofen 2.5 g, glycerol monolaurate 0.5 g and Kollidon 12 PF 0.3 g (BASF, Mw 2,000~3,000) were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 6>

The hydrophobic adhesive layer 2 was prepared with the same method as the embodiment 1. With respect to the drug adhesive layer 3 containing a drug, DuroTak 87-2074 5.3 g, DuroTak 87-2051 1 g, which were acrylic adhesives, ketoprofen 2.5 g, glycerol monolaurate 0.5 g, Kollidon 17 PF 0.3 g and polyethyleneglycol 600 0.4 g (Dow Chemical, Mn 560~640) were put in a beaker and stirred for one hour to prepare a solution having a uniform phase and then air bubbles were removed from the solution. The solution was coated on the silicon-treated polyester film so as to have a thickness of 50 μm after drying and then dried at 80° C. for 20 minutes. The film was separated from the hydrophobic adhesive layer pre-prepared, which was then put on the dried drug adhesive layer, thereby producing a patch (20×40 cm$^2$).

<Embodiment 7>

The hydrophobic adhesive layer 2 was prepared with the same method as the embodiment 1. With respect to the drug adhesive layer 3 containing a drug, DuroTak 87-2074 5.0 g, DuroTak 87-2051 1 g, which were acrylic adhesives, ketoprofen 2.5 g, glycerol monolaurate 0.5 g, Kollidon 17 PF 0.3 g and polyethyleneglycol 600 0.7 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 8>

The hydrophobic adhesive layer 2 was prepared with the same method as the embodiment 1. With respect to the drug adhesive layer 3 containing a drug, DuroTak 87-2074 5.7 g, DuroTak 87-2051 1 g, which were acrylic adhesives, ketoprofen 2.5 g, glycerol monolaurate 0.5 g, and polyethyleneglycol 600 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 9>

The hydrophobic adhesive layer 2 was prepared with the same method as the embodiment 1. With respect to the drug adhesive layer 3 containing a drug, DuroTak 87-2074 5.3 g, DuroTak 87-2051 1 g, ketoprofen 2.5 g, which were acrylic adhesives, glycerol monolaurate 0.5 g, and polyethyleneglycol 600 0.7 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm$^2$).

<Embodiment 10>

With respect to the hydrophobic adhesive layer 2, Kraton D1107 5 g (Shell Chemicals), which was a copolymer of styrene-isoprene-styren, Regalite R 1100 3 g (Eastman), which was hydrogenated petroleum resin, liquid paraffin 3 g and hexane 30 Ml were put in a beaker and stirred to prepare a uniform solution. The solution was coated on a silicon-treated polyester film so as to have a thickness of 50 μm after drying and then dried at 60° C. for 10 minutes. After that, the prepared hydrophobic adhesive layer was covered with the flexible backing 1 (flexible polyester woven-fabric), which was then pressed with a roll. With respect to the drug adhesive layer 3 containing a drug, DuroTak 87-2074 5.7 g, which was an acrylic adhesive, Gelva 788 1 g (Solutia Co., Ltd.), ketoprofen 2.5 g, glycerol monolaurate 0.5 g and Kollidon 17 PF 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 11>

With respect to the hydrophobic adhesive layer 2, Kraton D 101 5 g, which was a copolymer of styrene-isoprene-styrene, Regalite R 1100 3 g (Eastman), which was hydrogenated petroleum resin, liquid paraffin 3 g and hexane 30 Ml were put in a beaker and stirred to prepare a uniform solution. The solution was coated on a silicon-treated polyester film so as to have a thickness of 50 μm after drying and then dried at 60° C. for 10 minutes. After that, the prepared hydrophobic adhesive layer was covered with the flexible backing 1 (urethane), which was then pressed with a roll. With respect to the drug adhesive layer 3 containing a drug, DuroTak 87-2074 5.7 g, DuroTak 2051 1 g, which were acrylic adhesives, ketoprofen 2.5 g, glycerol monolaurate 0.5 g and Kollidon 17 PF 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 12>

The hydrophobic adhesive layer 2 was prepared with the same method as the embodiment 1. With respect to the drug adhesive layer 3 containing a drug, DuroTak 87-2074 5.3 g, DuroTak 87-2852 3 g, which were acrylic adhesives, ketoprofen 2.5 g, glycerol monolaurate 0.5 g, kollidon 17 PF 0.1 g and polyethyleneglycol 600 0.4 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 13>

The hydrophobic adhesive layer 2 was prepared with the same method as the embodiment 1. With respect to the drug adhesive layer 3 containing a drug, Gelva 737 6.7 g (Solutia, Co., Ltd.), which was an acrylic adhesives, ketoprofen 2.5 g, glycerol monolaurate 0.5 g and Kollidon 17 PF 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 14>

The hydrophobic adhesive layer 2 was prepared with the same method as the embodiment 1. With respect to the drug adhesive layer 3 containing a drug, DuroTak 87-2074 7.1 g, which was an acrylic adhesives, ketoprofen 2.2 g, propyleneglycol monolaurate 0.5 g, and Kollidon 17 PF 0.2 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 15>

The hydrophobic adhesive layer 2 was prepared with the same method as the embodiment 1. With respect to the drug adhesive layer 3 containing a drug, DuroTak 87-2074 6.8 g, which was an acrylic adhesives, ketoprofen 2.2 g, propyleneglycol monolaurate 0.5 g, and Kollidon 17 PF 0.5 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 16>

The hydrophobic adhesive layer 2 was prepared with the same method as the embodiment 1. With respect to the drug adhesive layer 3 containing a drug, DuroTak 87-2074 6.8 g, which was an acrylic adhesives, ketoprofen 2.2 g, propyleneglycol monolaurate 0.5 g, Kollidon 17 PF 0.2 g and polyethyleneglycol 600 0.3 g were put in a beaker and stirred for one hour to prepare a solution having a uniform phase and then air bubbles were removed from the solution. The solution was coated on the silicon-treated polyester film 4 so as to have a thickness of 40 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 17>

The hydrophobic adhesive layer 2 was prepared with the same method as the embodiment 1. With respect to the drug adhesive layer 3 containing a drug, DuroTak 87-2074 6.3 g, which was an acrylic adhesives, ketoprofen 2.8 g, glycerol monolaurate 0.5 g, and Kollidon 17 PF 0.4 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 18>

The hydrophobic adhesive layer 2 was prepared with the same method as the embodiment 1. With respect to the drug adhesive layer 3 containing a drug, DuroTak 87-2074 6.0 g, which was an acrylic adhesives, ketoprofen 2.8 g, glycerol monolaurate 0.5 g, and Kollidon 17 PF 0.7 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 19>

The hydrophobic adhesive layer 2 was prepared with the same method as the embodiment 1. With respect to the drug adhesive layer 3 containing a drug, DuroTak 87-2074 5.8 g, which was an acrylic adhesives, ketoprofen 2.8 g, glycerol monolaurate 0.5 g, Kollidon 17 PF 0.4 g and polyethyleneglycol 600 0.5 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 20>

The hydrophobic adhesive layer 2 was prepared with the same method as the embodiment 1. With respect to the drug adhesive layer 3 containing a drug, DuroTak 87-2074 5.7 g, DuroTak 87-2051 1 g, which were acrylic adhesives, diclofenac 2.5 g, glycerol monolaurate 0.5 g, Kollidon 17 PF 0.3 g and polyethyleneglycol 600 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 21>

The hydrophobic adhesive layer 2 was prepared with the same method as the embodiment 1. With respect to the drug adhesive layer 3 containing a drug, DuroTak 87-2074 5.7 g, DuroTak 87-2051 1 g, which were acrylic adhesives, flurbiprofen 2.5 g, glycerol monolaurate 0.5 g and Kollidon 17 PF 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

<Embodiment 22>

The hydrophobic adhesive layer 2 was prepared with the same method as the embodiment 1. With respect to the drug adhesive layer 3 containing a drug, DuroTak 87-2074 5.7 g, DuroTak 87-2051 1 g, which were acrylic adhesives, felbinac 2.5 g, glycerol monolaurate 0.5 g and Kollidon 17 PF 0.3 g were put in a beaker and stirred for one hour to prepare a solution having a uniform phase and then air bubbles were removed from the solution. The solution was coated on the silicon-treated polyester film 4 so as to have a thickness of 50 μm after drying and then dried at 80° C. for 20 minutes. The film was separated from the hydrophobic adhesive layer 2 pre-prepared, which was then put on the dried drug adhesive layer 3, thereby producing a patch (20×40 cm²).

The inventors conducted following tests so as to evaluate the effects of the transdermal preparations of the invention.

<Test 1> Assessment of the Transdermal Preparations: Skin Permeation Test

In order to assess the drug permeation of the patches prepared in the comparative examples and embodiments, the inventors cut the skin by 1.5×1.5 cm², which was cut in the abdominal region of a hairless mouse (female, 6 weeks), put it on a Franz-type diffusion cell, put the patches, which were prepared in the comparative examples and embodiments, on the skin and then fixed them with a clamp so that the patches were not moved. A phosphate buffer solution (pH 7.4) was put in a receptor part and a temperature of the diffusion cell was maintained at 37° C. The buffer solution of a receptor was stirred at a constant speed of 300 rpm, the whole receptor solution was taken after a predetermined time period has lapsed and the receptor was again filled with the buffer solution. The taken solution was analyzed with a high performance liquid chromatography. Each analysis condition of ketoprofen, diclofenac, flurbiprofen and felbinac was as follows.

[Ketoprofen]
column: YMC-Pack ODS-AM (1506.0 mm, I.D. 5 μm) (YMC Co., Ltd.)
mobile phase: 70:30 (V/V)=methanol:0.1% acetic acid aqueous solution
flow rate: 1 Me/min.
detection: UV wavelength 254 nm

[Diclofenac]
column: YMC-Pack ODS-AM (1506.0 mm, I.D. 5 μm)
mobile phase: 53:47 (V/V)=acetonitrile:0.02M acetic acid sodium buffer solution (pH 5.8)
flow rate: 1 Me/min.
detection: UV wavelength 280 nm

[Fluriprofen]
column: YMC-Pack ODS-AM (1506.0 mm, I.D. 5 μm)
mobile phase: 40:40:20(V/V/V)=acetonitrile:methanol: 0.5% acetic acid aqueous solution
flow rate: 1 Ml/min.
detection: UV wavelength 254 nm

[Felbinac]
column: YMC-Pack ODS-AM (1506.0 mm, I.D. 5 μm)
mobile phase: 38:62 (V/V)=acetonitrile:20 mM phosphate buffer solution (pH 7.4)
flow rate: 1 Ml/min.
detection: UV wavelength 254 nm The test results are showing a table 1. The table 1 shows in vitro permeability (hairless mouse skin, n=6) of the drug.

TABLE 1

| | Permeated amount for 6 hr (μg/cm²) | Permeated amount for 24 hr (μg/cm²) | Remark |
|---|---|---|---|
| comparative example 1 | 64 ± 11 | 186 ± 16 | — |
| comparative example 2 | 88 ± 9.0 | 243 ± 27 | Drug crystal was produced |
| comparative example 3 | 95 ± 13 | 279 ± 28 | Drug crystal was produced |
| comparative example 4 | 114 ± 21 | 307 ± 49 | — |
| comparative example 5 | 127 ± 14 | 359 ± 26 | PVP small particles were distributed in the adhesive layer |
| comparative example 6 | 151 ± 15 | 442 ± 37 | — |
| embodiment 1 | 227 ± 25 | 842 ± 38 | — |

TABLE 1-continued

|  | Permeated amount for 6 hr (μg/cm$^2$) | Permeated amount for 24 hr (μg/cm$^2$) | Remark |
|---|---|---|---|
| embodiment 2 | 188 ± 21 | 564 ± 36 | — |
| embodiment 3 | 215 ± 18 | 810 ± 33 | — |
| embodiment 4 | 228 ± 21 | 827 ± 51 | — |
| embodiment 5 | 219 ± 24 | 787 ± 29 | — |
| embodiment 6 | 248 ± 29 | 959 ± 34 | — |
| embodiment 7 | 189 ± 17 | 698 ± 43 | — |
| embodiment 8 | 224 ± 33 | 792 ± 28 | — |
| embodiment 9 | 216 ± 19 | 552 ± 19 | — |
| embodiment 10 | 209 ± 26 | 796 ± 42 | — |
| embodiment 11 | 216 ± 22 | 804 ± 29 | — |
| embodiment 12 | 233 ± 31 | 924 ± 35 | — |
| embodiment 13 | 213 ± 25 | 807 ± 41 | — |
| embodiment 14 | 217 ± 16 | 729 ± 49 | — |
| embodiment 15 | 165 ± 13 | 529 ± 29 | — |
| embodiment 16 | 246 ± 19 | 926 ± 31 | — |
| embodiment 17 | 242 ± 38 | 891 ± 44 | — |
| embodiment 18 | 201 ± 32 | 612 ± 47 | — |
| embodiment 19 | 271 ± 45 | 1021 ± 56 | — |
| embodiment 20 | 219 ± 14 | 843 ± 38 | diclofenac |
| embodiment 21 | 208 ± 26 | 798 ± 44 | flurbiprofen |
| embodiment 22 | 217 ± 29 | 766 ± 31 | felbinac |

As shown in the table 1, according to the result of the drug permeability, as the content of the drug in each formulation was increased, the contents of the polyvinyl pyrrolidone and polyethyleneglycol should be correspondingly increased to increase the drug permeation (embodiments 6, 16 and 19). When the content of the polyvinyl pyrrolidone or polyethyleneglycol exceeded a proper amount, the drug permeation was on the contrary decreased (embodiments 2, 7, 9, 15 and 18).

In the mean time, when the thickness of the hydrophobic adhesive layer 2 was less than 40 μm (comparative example 6), the drug permeation was low even though the ratio of the content of the drug to the content of the polymer resin belonged to an appropriate range.

<Test 2> Method of Assessing the In Vivo Permeability of the Drug and Water Content In order to assess the in vivo drug permeation of the patches prepared according to the comparative examples 1~6 and the embodiments 1, 2, 6, 7 and 14~19, each circular patch, which was cut to have a diameter of 3.5 cm, was attached to the upper arm of an adult human for 12 and 24 hours and then detached. After that, the content of drug remained in the patch was compared with the initial content thereof, thereby quantifying the content of drug permeated through the skin. The result is shown in a table 2. The analysis conditions of each drug were same as the test 1.

In order to measure the water content, which was an amount of water absorbed to the patch after the attachment, one patch was attached to the back region for 24 hours and then the initial weight of the patch before the attachment and the weight after the attachment for 24 hours were measured to calculate the water content after the attachment for 24 hours, with a following equation 4.

$$\text{water content}(\%) = \frac{W_{24hr} - W_{0hr}}{W_{0hr}} * 100 \quad <\text{equation 4}>$$

$W_{0hr}$: weight of the patch before the attachment $W_{24hr}$: weight of the patch after the attachment for 24 hours The result is shown in a table 2. The table 2 shows the in vivo drug permeation and the water content after the attachment for 24 hours.

TABLE 2

|  | Permeated amount for 12 hr (μg/8.042 cm$^2$) | Permeated amount for 24 hr (μg/8.042 cm$^2$) | Water content after the attachment for 24 hours (%) |
|---|---|---|---|
| comparative example 1 | 478 ± 27 | 712 ± 45 | 0.4 ± 0.2 |
| comparative example 2 | 524 ± 19 | 887 ± 33 | 0.4 ± 0.3 |
| comparative example 3 | 485 ± 23 | 793 ± 41 | 0.9 ± 0.1 |
| comparative example 4 | 519 ± 21 | 876 ± 37 | 3.6 ± 0.7 |
| comparative example 5 | 792 ± 24 | 1112 ± 31 | 4.2 ± 0.4 |
| comparative example 6 | 712 ± 27 | 1008 ± 39 | 2.1 ± 0.3 |
| embodiment 1 | 892 ± 38 | 1778 ± 48 | 3.1 ± 0.4 |
| embodiment 2 | 721 ± 32 | 1416 ± 42 | 3.8 ± 0.2 |
| embodiment 6 | 994 ± 31 | 1832 ± 34 | 4.1 ± 0.4 |
| embodiment 7 | 721 ± 42 | 1526 ± 45 | 4.7 ± 0.3 |
| embodiment 14 | 865 ± 41 | 1757 ± 61 | 2.9 ± 0.5 |
| embodiment 15 | 698 ± 38 | 1521 ± 58 | 3.1 ± 0.4 |
| embodiment 16 | 978 ± 45 | 1984 ± 51 | 4.3 ± 0.5 |
| embodiment 17 | 996 ± 52 | 2012 ± 46 | 3.0 ± 0.3 |
| embodiment 18 | 711 ± 38 | 1418 ± 21 | 3.6 ± 0.4 |
| embodiment 19 | 961 ± 54 | 2098 ± 68 | 4.9 ± 0.6 |

As can be seen from the table 2, the patch having an optimized combination ratio of the drug and the polyvinyl pyrrolidone or polyethyleneglycol, which was the hydrophilic polymer, exhibited the high drug permeability in the in vivo drug permeation test (embodiments 1, 6, 14, 16, 17 and 19). To the contrary, as the embodiments 2, 7, 15 and 18, the drug permeation was not highly increased in the description having the polyvinyl pyrrolidone exceeding the proper amount. That is, it is assumed that the affinity between the drug and the hydrophilic polymers is strong, so that the chemical activity of the drug is not highly increased, even though the environment was changed into hydrophilic by the water absorption from the skin.

[Test 3] Skin Irritation Test

In order to check the skin irritation of the patches prepared in the embodiments 1, 6, 14, 17, 19 and the like, the prepared patch was cut into a size of 2×2 cm$^2$, which was then attached to the forearm region of 10 human adult males. After 24 hours, the patch was removed. Then, after one hour, a primary irritation index of the attached region was determined according to a following determination criterion and a reaction degree of the skin was calculated from an equation 5.

<Determination Criterion>

TABLE 3

| Determination level | Irritation level |
| --- | --- |
| 0 | No Irritation |
| 1 | Minimum Irritation |
| 2 | Weak Irritation (erythema) |
| 3 | Severe Irritation (erythema, edema) |
| 4 | Extreme Irritation (erythema, edema) | reaction degree(%)={(sum of determination level× number of determinators)/(number of tested persons×4)}×100.   <equation 5>

As ea conversion result of the equation 5, the skin reaction degrees of the patches prepared in the embodiments 1, 6, 14, 17 and 19 were respectively 0.8, 0.7, 0.6, 0.9 and 0.8%. In other words, they little caused the skin irritation. Accordingly, when applying the patch to the skin, it is expected that the skin side effect is very little.

[Test 4] Adhesion Test

In order to assess the adhesive force of the patches containing the non-steroidal anti-inflammatory drug prepared in the embodiments 1, 2, 6, 7 and 14~19, the patch was cut to have a length of 20 cm and an area of 2.5 cm², thereby preparing a sample. Then, the patch was attached to a stainless steel plate in a longitudinal direction thereof and the attached patch was adhered by reciprocating a roll (500 g) two times. After leaving the patch at it was for 30 minutes, an adhesion tester (Texture analyzer Model XT2i, Stable Micro System) was used to measure an adhesion when releasing the patch with a degree of 180 at a speed of 300 mm/minute under conditions of 20° C. and a relative humidity of 65%. The result is shown in a table 4 (n=3).

TABLE 4

| | Adhesive force (g/25 mm) |
| --- | --- |
| comparative example 1 | 412 ± 27 |
| comparative example 2 | 417 ± 21 |
| comparative example 3 | 508 ± 18 |
| comparative example 4 | 418 ± 16 |
| comparative example 5 | 347 ± 26 |
| comparative example 6 | 398 ± 14 |
| embodiment 1 | 627 ± 17 |
| embodiment 2 | 562 ± 22 |
| embodiment 6 | 678 ± 19 |
| embodiment 7 | 517 ± 23 |
| embodiment 14 | 713 ± 18 |
| embodiment 15 | 658 ± 25 |
| embodiment 16 | 742 ± 42 |
| embodiment 17 | 706 ± 31 |
| embodiment 18 | 516 ± 15 |
| embodiment 19 | 487 ± 27 |

As shown in the table 4, the patches of the embodiments exhibited the adhesion more excellent than these of the comparative example. That is, the respective components are constituted with a proper combination ratio in the drug layer providing the adhesion, so that there occurs no phase separation between the raw materials, thereby exhibiting the excellent adhesion.

While the invention has been shown and described with reference to certain preferred embodiments thereof, it will be understood by those skilled in the art that various changes in form and details may be made thereto without departing from the spirit and scope of the invention as defined by the appended claims.

INDUSTRIAL APPLICABILITY

As described above, when the transdermal preparation of the invention is used, it is possible to provide a transdermal preparation capable of enabling the hydrophobic drug of a high concentration to be continuously permeated through the skin until the patch is detached from the skin. The transdermal preparation of the invention can minimize the skin side effect and improve the adhesive force.

The invention claimed is:

1. A transdermal preparation of a layered structure for a non-steroidal anti-inflammatory drug comprising:
   a backing layer (1) located at the highest part of the layered structure and having a flexibility;
   a hydrophobic adhesive layer (2) placed below the backing layer; and
   a drug adhesive layer (3) placed below the hydrophobic adhesive layer,
   wherein the hydrophobic adhesive layer (2) is free of the drug and contains a hydrophobic adhesive to prevent water absorbed from skin from being lost and the drug contained in the drug adhesive layer (3) from being reverse-transferred to the backing layer (1),
   wherein the hydrophobic adhesive is selected from a group consisting of a polyisobutylene adhesive, a styrene-isoprene-styrene adhesive and a styrene-butadiene-styrene adhesive,
   wherein the drug adhesive layer (3) contains the non-steroidal anti-inflammatory drug, an acrylic adhesives for adhering the transdermal preparation to the skin and a hydrophilic polymer resin for promoting the water absorption from the skin,
   wherein the hydrophilic polymer resin is polyvinyl pyrrolidone or polyethyleneglycol, the total drug adhesive layer comprising 0.2-6 wt % polyvinyl pyrrolidone when the hydrophilic polymer resin is polyvinyl pyrrolidone, or 1-8 wt % polyethyleneglycol when the hydrophilic polymer resin is polyethyleneglycol, and
   wherein the non-steroidal anti-inflammatory drug is one or more selected from a group consisting of ketoprofen, diclofenac, flurbiprofen and felbinac.

2. The transdermal preparation according to claim 1, further comprising a release layer (4) placed below the drug adhesive layer, protecting the drug adhesive layer until the transdermal preparation is used and released when the preparation is used.

3. The transdermal preparation according to claim 1, wherein the hydrophobic adhesive layer has a thickness of 40-100 μm.

4. The transdermal preparation according to claim 1, wherein the non-steroidal anti-inflammatory drug of the drug adhesive layer is contained in an amount of 10-40 wt % for a total drug adhesive layer.

5. The transdermal preparation according to claim 1, wherein the polyvinyl pyrrolidone has a molecular weight of 1,000-50,000.

6. The transdermal preparation according to claim 1, wherein the polyethyleneglycol has a molecular weight of 400-8,000.

7. The transdermal preparation according to claim 1, wherein the hydrophilic polymer resin of the drug adhesive layer is contained in an amount of 10 wt % or less for a total drug adhesive layer.

8. The transdermal preparation according to claim 1, wherein the acrylic adhesives of the drug adhesive layer are contained in an amount of 40-80 wt % for a total drug adhesive layer.

9. The transdermal preparation according to claim 1, wherein the drug adhesive layer further comprises a permeation enhancer for enhancing the drug permeation, and
- wherein the permeation enhancer is a long chain fatty acid having a carbon number of 10-18 and derivatives thereof which are used in an individual or mixture form,
- the fatty acid derivative being selected from a group consisting of lauryl alcohol, oleyl alcohol, sorbitan monolaurate, polyethyleneglycol monolaurate, propyleneglycol monolaurate, glycerin monolaurate, caprylic monolaurate and isopropyl myristate, and
- the permeation enhancer is contained in an amount of 3~20 wt % for a total drug adhesive layer.

10. The transdermal preparation according to claim 1, wherein the backing layer is made of a woven or non-woven fabric having a unidirectional or dual directional flexibility, and wherein the woven fabric consists of a polyester based resin, urethane based resin or cotton, and the non-woven fabric consists of the polyester based resin or urethane based resin.

* * * * *